United States Patent
Hoffmann et al.

(10) Patent No.: US 6,190,689 B1
(45) Date of Patent: *Feb. 20, 2001

(54) HYDROPHILIC PRESSURE SENSITIVE HOT-MELT ADHESIVES

(75) Inventors: Hans-Rainer Hoffmann; Michael Roreger, both of Neuwied (DE)

(73) Assignee: LTS Lohmann Therapie-Systeme GmbH, Neuwied (DE)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/737,224
(22) PCT Filed: May 8, 1995
(86) PCT No.: PCT/EP95/01724
§ 371 Date: Nov. 13, 1996
§ 102(e) Date: Nov. 13, 1996
(87) PCT Pub. No.: WO95/31188
PCT Pub. Date: Nov. 23, 1995

(30) Foreign Application Priority Data

May 13, 1994 (DE) ................................. 44 16 927

(51) Int. Cl.⁷ ..................................................... A61F 13/02
(52) U.S. Cl. ........................... 424/448; 424/447; 424/449
(58) Field of Search ........................................ 424/447, 448, 424/449

(56) References Cited

U.S. PATENT DOCUMENTS

| | | | |
|---|---|---|---|
| 4,842,864 | * | 6/1989 | Guillemet .............................. 424/448 |
| 5,456,745 | * | 10/1995 | Roreger ................................. 106/128 |
| 5,629,003 | * | 5/1997 | Horstmann ............................ 424/401 |

FOREIGN PATENT DOCUMENTS

| | | | |
|---|---|---|---|
| 4230588 | * | 10/1993 | (DE) .............................. A61L/15/44 |
| 0355536 | * | 2/1990 | (EP) ................................ C08J/5/18 |
| 0507160 | * | 10/1992 | (EP) ............................. A61K/31/165 |
| 2612785 | * | 9/1988 | (FR) ............................. A61K/31/565 |
| 87/02870 | * | 5/1987 | (WO) ............................. A24F/47/00 |

* cited by examiner

Primary Examiner—Gollamudi S. Kishore
Assistant Examiner—Lakshmi Channavajjala
(74) Attorney, Agent, or Firm—Wenderoth, Lind & Ponack, L.L.P.

(57) ABSTRACT

A device for the release of substances from pressure sensitive hot-melt adhesives with a uniform or non-uniform distribution of said substances is characterized by the fact that the pressure sensitive hot-melt adhesive is hydrophilic and comprises at least one water-soluble, or at least water-swellable, polymer, at least one water-soluble, meltable adhesive resin, as well as substance to be released.

24 Claims, 2 Drawing Sheets

HYDROPHILIC PRESSURE SENSITIVE HOT-MELT ADHESIVES

SPECIFICATION

The present invention relates to devices for the release of substances from pressure sensitive hot-melt adhesives having an uneven or even distribution of the substances.

Typical representatives of devices for the release of substances from adhesives are self-adhesive products for the application on intact skin, for example, medicinal patches for the controlled dermal or transdermal release of substances and cosmetic patches for the release of active or odorous substances; self-adhesive products for the application on injured skin, e.g., patches, wound dressings, or surgical films for the release of substances to wounds.

Pressure sensitive adhesive layers comprising pharmaceutical or other active substances are for the most part formed by coating a solution or dispersion with subsequent evaporation of the solvent or dispersant.

The use of solvents or dispersing agents in the production of adhesive layers for devices of the above-mentioned type is disadvantageous for many reasons; this applies to both the economic point of view because of expensive drying lines, extracting plants, recovery and disposal facilities, and to the ecological point of view because of the environmental impact caused by solvents and dispersing agents as well as their degradation products.

In contrast to this, adhesive layers manufactured from a melt of the formulation components have advantages with respect to economy and ecology. However, there is the disadvantage that very high temperatures are necessary to melt the commonly used pressure sensitive hot-melt adhesive formulations so that the pharmaceutical or other active substances to be incorporated are decomposed, modified or evaporated, at least partially.

In addition, the conventional pressure sensitive hot-melt adhesive formulations—as well as adhesive formulations bound by solvents or dispersants—have further disadvantages, in particular when used in man; in general, these become apparent in the form of skin reactions and painful rubors during the application or after removal of the device.

In case of aggressively adhering devices, these skin irritations may be due to an injury of the corneum when the adhesive device is removed from the skin. Most frequently, however, skin reactions result from the fact that the base components of adhesive formulations are of a lipophilic nature; this in particular applies to pressure sensitive adhesives. When applied to the skin, these adhesives have the effect of occlusive films or foils which completely prevent the cutaneous respiration and evaporation of water and thus suppress the mechanisms of thermoregulation at the application site. Since the water released by the skin cannot evaporate, thin water films and water islands form between the adhesive layer and the skin and these represent an optimum environment for the growth and multiplication of skin germs. Once a certain population size is reached, the amount of skin germs decomposing per time unit is such that the concentration of toxic catabolic products and decomposition products drastically increases, again resulting in massive skin reactions.

There were attempts to combat these phenomena, e.g., in case of the pressure sensitive adhesive formulation for self-adhesive wound dressings, by incorporating so-called hydrocolloidal particles into pressure sensitive hot-melt adhesives, i.e., hydrophilic substances, in particular polymers, which absorb and withdraw water from the surface of the skin.

But even these formulations cannot avoid another serious disadvantage of conventional pressure sensitive hot-melt adhesives. In addition to the above-mentioned, rather physical reasons resulting in skin irritations, it is first of all the allergic skin reactions that cause problems, and these are usually caused by the chemical properties of the lipophilic adhesive resins used. Up to the present, this problem has not been solved satisfactorily, since these adhesive resins cannot be omitted when a reliable adherence to the skin is required.

Owing to their lipophilic nature, prior art pressure sensitive hot-melt adhesive formulations for the release of substances have another disadvantage: with respect to the controlled release of substances they are suitable only for lipophilic substances. In the case of hydrophilic substances it is hardly possible to create the preconditions for the release control relating to the thermodynamic activity in the pressure sensitive hot-melt adhesive. These substances must be dissolved in the adhesive formulation, at least partially, so that they can diffuse within an adhesive formulation, reach the interface and be released; in general, this cannot be achieved when hydrophilic substances and lipophilic pressure sensitive hot-melt adhesives are combined.

Accordingly, it was the object of the present invention to find a device for releasing substances from pressure sensitive hot-melt adhesives, which comprises a pressure sensitive hot-melt adhesive that reliably adheres to the desired surface at room temperature after slight pressure, does not leave any residue on the surface after removal, absorbs cutaneous moisture, comprises non-allergenic adhesive resins, and permits the incorporation of hydrophilic substances in dissolved form.

In a device for the release of substances from hydrophilic pressure sensitive hot-melt adhesives having an even or uneven distribution of these substances, this object is achieved with the present invention by the fact that the pressure sensitive hot-melt adhesive is hydrophilic and comprises at least one water-soluble or at least water-swellable polymer, at least one water-soluble, meltable adhesive resin, and substance to the released.

Most surprisingly, it turned out that it is possible to produce pressure sensitive hot-melt adhesives complying with the above-mentioned requirements by combining water-soluble, or at least water-swellable, polymers with water-soluble, meltable adhesive resins under addition of the substances to be released; and in this connection water-soluble, meltable tacky substances, which are low-viscous and ropy per se—when combined with hydrophilic polymers—form coherent layers of an excellent cohesion which, in addition to that, have adhesive forces absolutely comparable to those of conventional adhesives.

Pressure sensitive hot-melt adhesives within the meaning of the present invention are those by means of which coated devices can reliably be joined with surfaces at room temperature under slight pressure, and which have a cohesion permitting a residual-free removal of the adhesive-coated device from the application surface by simply stripping it off. In order to avoid undesired modifications of the substances to be released or of other formulation components, the pressure sensitive hot-melt adhesives of the kind specified herein are preferably processed at temperatures between 40 and 150° C., most preferably at temperatures between 80 and 120° C., in molten condition, and they solidify under formation of adhesive and cohesive forces.

Pressure sensitive hot-melt adhesives of the type mentioned herein differ greatly from hydrophilic, water-soluble adhesives known from the production of so-called gummed surfaces, e.g., envelopes or labels. These adhesives which build up cohesive but no adhesive forces after melting, processing, and setting are activated only when moistened with water or saliva, and they are brought into contact with the application surface in moist condition. After drying of the adhesive, adhesive forces build up which firmly join the respective surfaces, e.g., paper labels with glass surfaces. In contrast to surfaces joined by pressure sensitive hot-melt adhesives, said adhesive forces between device and surface cannot be eliminated by simply pulling the adhesive-coated device off the application surface; in these cases neutralization of the adhesive forces can only be effected by redissolving or slightly solving the adhesive, e.g., by moistening with water, removal in a water-bath or over water vapor.

When formulating the pressure sensitive hot-melt adhesives according to the present invention, the main problem was to find substances which are water-soluble and meltable in addition, have adhesive properties at room temperature, and are known not to cause skin irritations or allergic reactions even in case of a prolonged application on human skin. These substances are very rare, and so far they are to be found in particular among the natural substances. Such tackifying substances which, following the existing terminology, are referred to as adhesive resins preferably are pantothenyl alcohol, honey, low-molecular sugars, such as saccharose, glucose and fructose, or derivatives of low-molecular sugars, such as saccharose acetate isobutyrate, as well as combinations thereof.

Suitable water-soluble or water-swellable polymers within the meaning of the present invention include any hydrophilic natural, semi-synthetic or synthetic polymer which melt at the applied temperatures or which—at least partially—dissolve in dry or pre-swollen form in the adhesive resin melts used. These preferably include gelatin, vegetable polysaccharides, such as alginates, pectins, carrageenans, or xanthan; cellulose derivatives, such as methyl cellulose, hydroxypropylcellulose, hydroxyethylcellulose, hydroxypropyl methylcellulose, or sodium carboxymethylcellulose; starch and starch derivatives, galactomannan and galactomannan derivatives, polyvinyl alcohol, polyvinylpyrrolidone, vinyl-pyrrolidone-vinyl-acetate-copolymers, polyethylene glycols, and polypropylene glycols.

In connection with the present invention, the term "substances" is to be understood as chemical elements, organic and inorganic compounds which, in a generic device, are capable of migrating out of the components comprising them, thus causing a desired effect. Among the fields of application of the device according to the present invention, human and veterinary medicine, as well as the application to plants are of special importance, with an embodiment of the present invention in the form of a patch being particularly preferred.

The device according to the present invention for the release of substances from pressure sensitive hot-melt adhesives is applied, for example, on intact skin or on wounds. In these cases the substances to be released preferably serve the dermal treatment of topical skin diseases, the intradermal or transdermal treatment of diseases, the treatment of wounds, or the skin care in cosmetic preparations.

For the dermal treatment of local skin diseases the following substances are used: local anaesthetics, local antibiotics, antiseptics, antimycotics, antihistaminics, and antipruritic drugs; keratolytics and caustic drugs; virustatics, antiscabietic agents, steroids, as well as different substances for the treatment of acne, psoriasis, or photodermatoses. Active substances applied intradermally include, for example, steroid and non-steroid antirheumatics, local anaesthetics, substances stimulating the blood flow, or vasoprotectors and vasoconstrictors for the treatment of vascular diseases, as well as active substances to influence the processes in the subcutaneous fatty tissue. The active substances applied transdermally include, for example, neuroleptics, antidepressants, tranquilizers, hypnotics, psychostimulants, analgesics, cytostatic drugs, hormones, muscle relaxants, antiparkinson drugs, ganglionic blockers, sympathomimetics, alpha-sympatholytics, betasympatholytics, antisympathotonics, antidiabetics, coronary therapeutic agents, antihypertensives, anti-asthmatics, diuretics, or active substance for weight reduction.

For the treatment of wounds styptic active substances are used, for example, collagen, wound-cleansing substances, such as enzymes, antiseptics, disinfectants, and antibiotics; pain-relieving agents and anaesthetic active substances, as well as active substances promoting wound healing to stimulate granulation, to induce vascularization, or to promote epithelization.

In a preferred embodiment for the transdermal application, the hydrophilic pressure sensitive hot-melt adhesive comprises actetylsalicylic acid, preferably for the antithrombotic therapy, i.e., for the prevention of a first cardiac infarction, for the prevention of a recurrent infarction, for the treatment of unstable angina pectoris, for the thrombosis prophylaxis after transplantation of vascular protheses or artificial heart valves, for the thrombosis prophylaxis of the peripheral arterial vessels, as well as for the thrombosis prophylaxis of cerebral inadequate circulation.

According to another preferred embodiment for the transdermal application, the hydrophilic pressure sensitive hot-melt adhesive comprises a steroid hormone, preferably estradiol; when applied transdermally this is used for hormone substitution during the postmenopause or for the treatment of osteoporosis. On the other hand, a device for the release of estradiol from hydrophilic pressure sensitive hot-melt adhesives may also be applied on long-term wounds, for instance crural ulcera, for the treatment of wounds.

In a preferred embodiment for the intradermal application of active substances, the hydrophilic pressure sensitive hot-melt adhesive comprises an eutectic mixture of the local anaesthetics, lidocaine and prilocaine. Both in the intradermal analgesia, for example prior to venipunctures, and in the treatment of rheumatoid arthritis, this active substance mixture may achieve an effect which cannot be obtained by means of the conventionally used active substances and active substance combinations from the group of topical anaesthetics.

According to another preferred embodiment of the device according to the present invention, the hydrophilic pressure sensitive hot-melt adhesive comprises vegetable preparations, e.g., extracts or tinctures. These may be used for the treatment of topical skin diseases, for example, oak bark extract, walnut extract, tincture of arnica, hamamelis extract, ribwort extract, pansy extract, thyme or sage extract; for the treatment of damaged or injured skin, for example, St. John's wort tincture, cone flowers tincture, chamomile flowers extract, or calendula flowers tincture; and for the care of exhausted and damaged skin, for example, birch leaves extract, nettle extract, coldsfoot extract, comfrey tincture, horsetail extract, or aloe vera extract. Vegetable preparations may also be released from hydrophilic pressure sensitive hot-melt adhesives for the intradermal treatment of diseases, for example, extracts of horse chestnut and butcher's broom in case of vein diseases, or extracts and tinctures of arnica, calendula, and capsicum in case of contusions, distortions, or haemorrhages. Vegetable preparations in hydrophilic pressure sensitive hot-melt adhesives according to the present invention may also be used in the transdermal therapy, for example, ginseng extract in case of geriatric complaints; valerian tincture, extracts of melissa and hop to cause a sedative effect in case of superexcitation, sleep disturbances, and stress; extracts of kola and tea to achieve a stimulative effect; or hawthorn extract for the stabilization of the circulatory system.

In particular cases where the formulation components of the hydrophilic pressure sensitive hot-melt adhesive themselves are capable of extracting ingredients from parts of plants, the hydrophilic pressure sensitive hot-melt adhesive may also comprise triturated plant portions. According to a preferred embodiment, the hydrophilic pressure sensitive hot-melt adhesive of the device according to the present invention comprises tobacco powder. Such a device can be used by smokers as an alternative to tobacco, cigarettes or similar tobacco products. This substitute, e.g., for cigarettes, offers the advantage that the smoker himself does not inhale the injurious substances resulting during the combustion of tobacco without having to dispense with the desired effects of tobacco consumption, on the one hand, and that non-smokers are not subjected to the risks of passive smoking, on the other hand.

The device according to the present invention for the release of substances from hydrophilic pressure sensitive hot-melt adhesives may also be used on plants. For instance, superficial, locally limited plant diseases can be treated with active substances which are released from the hydrophilic pressure sensitive hot-melt adhesive to the plant surface. Also, active substances having a systemic effectiveness, which serve the protection of the plant from pathogenic agents and pests or the treatment of plants after infection and existing infestation, or which serve the growth control or the nutrition of the plant, can be released from the hydrophilic pressure sensitive hot-melt adhesive to the plant surface, e.g., to the leaves, the stem, or the roots. After release from the hydrophilic pressure sensitive hot-melt adhesive, the active substance penetrates into epidermal and subepidermal tissues of the plant, enters the transport systems of the plant, and is distributed in the plant systemically after absorption.

The systemic active substances may, for example, be fungicides, such as bitertanole, fenarimole, triforine, aluminiumfosetyl, or tridemorph; insecticides, such as nicotine, demeton, dimethoate, fenthion, or menazon; or plant hormones, such as auxins, gibberellins, cytikinins, or abscisic acid.

The base formulation and production of the device according to the present invention for the release of substances from pressure sensitive hot-melt adhesives with a uniform or non-uniform distribution of the substances, according to the features of the main claim are exemplified in the following:

EXAMPLE 1

100 parts of the water-soluble adhesive resin, pantothenyl alcohol, are melted at 70° C. 30 parts of polyethylene glycol having a molecular weight of 15,000 are slowly stirred into the melt until a clear melt results.

10 parts of sodium alginate and 1.5 parts of substance to be released, e.g., lidocaine hydrochloride, are slowly stirred into the melt until an even distribution is achieved.

Then, the pressure sensitive hot-melt adhesive is spread on a suitable substrate, e.g., a siliconized paper composite, by means of knife coating.

After cooling, a suitable backing layer, e.g., a thin polyester sheet, is laminated on the pressure sensitive hot-melt adhesive. Devices of desired size are punched from this laminate.

The pressure sensitive, hydrophilic contact adhesive of the device according to the present invention thus manufactured has an excellent initial tackiness when applied to the skin, an excellent adhesion during the wearing duration, and an excellent cohesion when stripped off the skin so that the device can be removed from the skin without leaving any residue. In addition, the device stands out for the fact that the hydrophilic pressure sensitive hot-melt adhesive absorbs cutaneous moisture, prevents the formation of water films promoting the growth of bacteria, does not cause any skin irritations or allergic reactions, and—owing to the absorption of cutaneous moisture—that it is soft and supple at the interface to the skin, permitting an easy and painless, residue-free removal from the skin without causing any damage to the corneum.

According to another preferred embodiment of the device according to the present invention for the release of substances from pressure sensitive hot-melt adhesives, said hydrophilic pressure sensitive hot-melt adhesive comprises 0.1% to 40% of water to influence the thermodynamic activity of the substance to be released.

EXAMPLE 2

20 parts of pantothenyl alcohol are melted at 90° C.; 10 parts of glycerol, 2 parts of Tween 20, 2 parts of ethylcellulose, and 1.5 parts of estradiol are slowly stirred into the melt until an even distribution is achieved (melt A).

18 parts of gelatin, 10 parts of polyvinyl pyrrolidone, 5 parts of sodium carboxymethylcellulose, and 11.5 parts of saccharose are made into a paste at room temperature using 20 parts of water, intensively homogenized up to an even distribution, and then heated to 90° C. under stirring (melt B).

Melt B is slowly stirred into melt A at 90° C. until a uniform distribution is achieved. Then, the pressure sensitive hot-melt adhesive is spread on a siliconized paper composite by means of a coating knife; after cooling, a polyester sheet is laminated thereon. Devices of the desired area are punched out of this laminate.

When applied to the skin, the pressure sensitive, hydrophilic hot-melt adhesive of the device according to the present invention thus manufactured meets the above-mentioned requirements with respect to initial tackiness, adherence during wearing, cohesion, absorption of cutaneous moisture, and the property of not irritating the skin. In addition, it has the advantage that—as compared to the known lipophilic transdermal systems—the thermodynamic activity of estradiol in the adhesive layer is significantly influenced due to the presence of water. This extends the possibilities of influencing and controlling the estradiol release from such a device. In addition, owing to the hydrophilic character, the described formulation has the advantage that when—used for the release of estradiol or other substances to wounds—an interaction with the wound exudate is possible, on the one hand, and that, on the other hand, the presence of water in the formulation creates a moist microclimate in the wound which promotes the healing processes in case there is no wound exudation.

According to another preferred embodiment of the device according to the present invention for the release of substances from pressure sensitive hot-melt adhesives, the hydrophilic pressure sensitive hot-melt adhesive comprises a lipophilic phase in order to influence the thermodynamic activity of the substance to be released.

EXAMPLE 3

27 parts of pantothenyl alcohol are melted at 90° C. 12.5 parts of sodium alginate, 12.5 parts of gelatin, and 1 part of chlorophyll are slowly stirred into the melt until a uniform distribution is achieved (melt A).

Separately, 25 parts of hydroabietyl alcohol are melted at 125° C. 10 parts of an ethylene-vinyl-acetate-copolymer having a vinyl acetate content of 28%, 10 parts of a polyalkadiene having a monomer chain length of C4 to C5, and 2 parts of lidocaine are slowly stirred into the hydroabietyl alcohol melt at 120° C. until a clear melt results (melt B).

Melt B is cooled to 90° C. under stirring; at 90° C. it is slowly stirred into melt A up to a uniform distribution. The pressure sensitive hot-melt adhesive is then spread on a siliconized paper composite by means of knife coating. After cooling, a polyester sheet is laminated thereon, and devices of desired size are punched from the laminate.

When applied to intact skin or wounds, the pressure sensitive, hydrophilic hot-melt adhesive of the device according to the present invention such manufactured—like the above-described device—meets the mentioned requirements with respect to initial tackiness, adhesion during wearing, cohesion, non-irritancy to the skin, and absorption or interaction with the wound exudate or cutaneous moisture.

The advantage of combining the hydrophilic base components of the device according to the present invention with lipophilic formulation components in a hydrophilic pressure sensitive hot-melt adhesive lies in the fact that even lipophilic substances which are to be released from the pressure sensitive hot-melt adhesive are present in an at least partially dissolved form; this is an important condition for the diffusion of the substance in the pressure sensitive hot-melt adhesive and thus for the release from the pressure sensitive hot-melt adhesive.

The lipophilic phase of the device according to the present invention may be non-separated and coherent, as in the above Example; however, it may also be present in a separated and incoherent state in the form of small particles or droplets.

Homo-, co- or block polymers may be used as components of the lipophilic phase, e.g., polyamides, polyesters, polycaprolactams, polycaprolactone, ethylene-vinyl-acetate copolymers (EVA), ethylene-ethyl-acrylate copolymers (EEA), polyvinyl ether, poly(meth)acrylates, polyvinyl acetals, polyvinyl acetates, styrenebutadiene-block polymers, isoprene block polymers, polyurethanes, ethylcellulose, cellulose-acetate-butyrate, synthetic rubbers (e.g. neoprene rubber), polyisobutylene, butyl-rubber, and acrylonitrile-butadiene copolymers or resins, such as epoxide resins, melamine resins, phenolformaldehyde resins, and resorcinolformaldehyde resins; among others the following modified resins may also be used: hydrogenated colophony, polymerized colophony, dimerized resin acids, disproportionated colophony, methyl esters of colophony, glycerol esters of hydrogenated colophony, methyl esters of hydrogenated colophony, pental esters, triethylene glycol esters of hydrogenated colophony, hydroabietyl alcohol and its derivatives, glycerol esters, di-triol esters, and pental esters of resin acids, pental esters of polymerized colophony, pental esters of dimerized colophony, glycerol esters of dimerized colophony, esters of colophony modified with maleic acid or phenol, aromatic and aliphatic hydrocarbon resins, hydrogenated resins, polyterpene resins and modified terpene resins.

However, the lipophilic phase may also consist of natural, semisynthetic or synthetic fats and oils, such as olive oil, castor oil, peanut oil, soy bean oil, linseed oil, sesame oil, jojoba oil, avocado oil, hydrogenated peanut oil, hydrogenated castor oil, triglyceride mixtures (Miglylol®, Softisan®), or silicone oils; natural, semisynthetic or synthetic waxes, such as beeswax, wool wax, earth wax, spermaceti, oleic acid oleyl ester, isopropyl palmitate, isopropyl myristate, ethyl oleate, cetyl palmitate, or cetyl stearate; fatty alcohols, such as dodecyl alcohol or cetyl alcohol; fatty acids, such as myristic acid, oleic acid, or linoleic acid; propoxylated, ethoxylated or sulfated fatty alcohols, fatty acid alkyl amides, fatty acid-protein-condensation products, phospholipids, sterols, or hydrocarbons, such as paraffins or paraffin oils. If the lipophilic phase is present in separated form, adjuvants, such as emulsifiers and/or protective colloids, are added to the preparation according to the present invention in order to stabilize the disperse phase.

In addition to the above-mentioned adjuvants, the device for the release of substances from hydrophilic pressure sensitive hot-melt adhesives may comprise as adjuvants:

humectants, such as glycerol, sorbitol, polyethylene glycol, polypropylene glycol, softening agents, such as citric acid ester, tartaric acid ester, or glycerol ester, penetration enhancers, such as alkyl sulfates, alkyl sulfonates, alkali soaps, fatty acid salts of multivalent metals, betaines, amine oxides, fatty acid esters, mono-, di- or triglycerides, long-chain alcohols, sulfoxides, nicotinic acid ester, salicylic acid, N-methyl pyrrolidone, 2-pyrrolidone, or urea, preservatives, such as p-Cl-m-cresol, phenylethyl alcohol, phenoxyethyl alcohol, chlorobutanol, 4-hydroxybenzoic acid methylester, 4-hydroxybenzoic acid propylester, benzalkonium chloride, cetylpyridinium chloride, chlorohexidine diacetate or gluconate, ethanol, or propylene glycol, disinfectants, for example, halogens, such as polyvidoneiodine; halogen compounds, such as sodium hypochloride or tosylchloride sodium; oxidants, such as hydrogen peroxide or potassium permanganate, aryl mercury compounds, such as phenylmercury borate or merbromin; alkyl mercury compounds, such as thiomersal; organotin compounds, such as tri-n-butyltin benzoate; silver protein compounds, such as silver protein acetyltannate; alcohols, such as ethanol, n-propanol, or isopropanol; phenols, such as thymol, o-phenylphenol, 2-benzyl-4-chlorophenol, hexachlorophene, or hexylresorcinol; or organic nitrogen compounds, such as 8-hydroxyquinoline, chloroquinaldol, clioquinol, ethacridine, hexetidine, chlorohexidine, or ambazone, pH-regulators, such as glycerol buffers, citrate buffers, borate buffers, phosphate buffers, or citric acid phosphate buffers, antioxidants, such as ascorbic acid, ascorbic palmitate, tocopherol acetate, propyl gallate, butylhydroxyanisole, or butylated hydroxytoluene, active substance stabilizers, such as mannitol, glucose, lactose, fructose, saccharose, odorous substances, dyes, cleaning agents, substances for personal hygiene, emulsion stabilizers, such as non-ionogenic emulsifiers, amphoteric emulsifiers, cation-active emulsifiers, and anion-active emulsifiers, fillers, such as micro-crystalline cellulose, aluminum oxide, zinc oxide, titanium oxide, talcum, silicon dioxide, magnesium silicate, magnesium aluminum silicate, kaolin, hydrophobic starch, calcium stearate, or calcium phosphate.

In addition to the knife coating procedures mentioned in the above Examples, processing of the active substance-releasing, hydrophilic pressure sensitive hot-melt adhesive layer may also be effected according to other methods known to those skilled in the art, e.g., roll coating, extrusion, casting, spraying, or printing. In many of these processes the limit of processibility of the hydrophilic pressure sensitive hot-melt adhesives is achieved at a viscosity in the range of about 80,000 Pa.

In case the support to be treated with the adhesive—a component of the device—could be damaged by the temperature of the adhesive which is applied in hot condition—be it by decomposition, reaction, or partial melting—a cooled support may be used. Cooling may be effected according to methods known per se, for instance, introduction of cold, inert gases or contact with a cooling surface.

When highly volatile and/or thermally instable substances are to be released, the following special measures may be suitable for processing:

A: Working at the lowest possible temperatures
B: Increasing the external pressure in order to decrease evaporation
C: Saturation of the vapor chamber above the melt with the vaporous substance
D: Working with the lowest possible amount of volatile substance in the melt, according to the instructions.

It goes without saying that these measures, for instance, working in an encapsulated unit, are limited by the laws known to the skilled artisan, both with respect to the intended use of the device to be manufactured and to the material conditions.

Devices according to the present invention wherein the active substance-releasing portion of the device comprises hydrophilic pressure sensitive hot-melt adhesives may be built-up according to any patch construction known to those skilled in the art. Basic types of such constructions include, for example, the membrane system and the matrix system.

Figure 1:
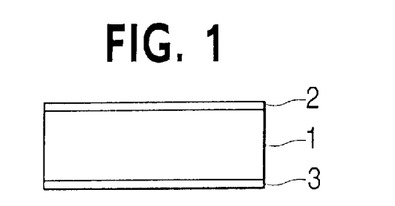
FIG. 1 represents a hydrophilic pressure sensitive hot-melt adhesive (1) provided with an impermeable backing layer (2) on one side and with a removable, impermeable protective layer (3) on the opposite side.

A membrane system comprises at least 5 parts: a flexible backing layer, an active substance-containing, pressure sensitive hot-melt adhesive, a membrane for controlling the active substance release, an adhesive layer laminated on said membrane for fixing the system to the skin, as well as a removable protective layer covering the adhesive surface of the patch facing the skin. A matrix system (FIG. 1) of the most simple type comprises three parts: a flexible backing layer, an active substance-containing, hydrophilic pressure sensitive hot-melt adhesive, and a removable protective layer which covers the adhesive surface of the device facing the skin.

A process for the production of a device according to the present invention of the type matrix system comprises continuous or discontinuous application of molten, hydrophilic pressure sensitive hot-melt adhesive, which comprises the substance to be released, at a temperature of the pressure sensitive hot-melt adhesive between 40 and 150° C., preferably 80 to 120° C., onto a flexible backing layer, and optional provision of the protective layer material.

Another process comprises continuous or discontinuous application of molten, hydrophilic pressure sensitive hot-melt adhesive, which comprises the substance to the released, at a temperature of the pressure sensitive hot-melt adhesive between 40 and 150° C., preferably 80 to 120° C., onto a protective layer material, and optional provision of the flexible backing layer. The hydrophilic pressure sensitive hot-melt adhesive may be applied to the protective layer or backing layer, for example, in the form of layers or in individual regions according to a predetermined pattern.

Suitable materials for the flexible backing layer include, for example, polyester, polyamide, polyethylene, polypropylene, polyurethane, polyvinyl chloride, both as so-called "solo-films" and as sandwich films in a combination of films of different of these plastic materials. In addition, these sheets may be aluminized or laminated with an aluminum foil.

Suitable materials for the removable protective layer include, for example, polyester, polyethylene, polypropylene, and papers coated with said materials and optionally aluminized or laminated with an aluminum foil. Additionally, the films or papers are coated with silicone in order to render them removable.

Depending on the intended use, for example, when the substance to be released is to be delivered through the backing layer, e.g., in case of essential oils, the pressure sensitive hot-melt adhesive may be provided with a backing layer which is permeable to the substance/s to be released; whereas a backing layer which is impermeable to the substance to be released is preferred in the embodiment of the device as a transdermal system where the substance is to be released to the skin only.

During the melting of the formulation components of the hydrophilic pressure sensitive hot-melt adhesive air may be stirred into the mass so that the hydrophilic pressure sensitive hot-melt adhesive obtained after spreading or casting will have a porous structure. The production and stabilization of the porous structure may be supported, for example, by adding foaming agents, such as saponins, alginic esters, amine oxides, or fatty amine oxides.

The composition of the device according to the present invention as a whole or that of the hydrophilic pressure sensitive hot-melt adhesive may be chosen such that the hydrophilic pressure sensitive hot-melt adhesive be biodegradable. Biodegradability is meant to be understood, for example, as the effect of UV-light, the action of microbes, or the action of enzymes.

Figure 2:
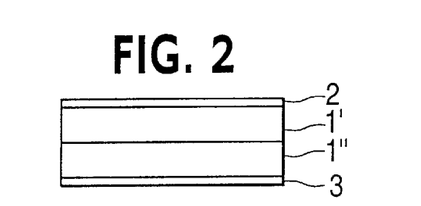
FIG. 2 illustrates a multi-layer, hydrophilic pressure sensitive hot-melt adhesive (laminate) wherein the hydrophilic pressure sensitive hot-melt adhesive (1) is divided into two layers (1', 1").
Figure 3:
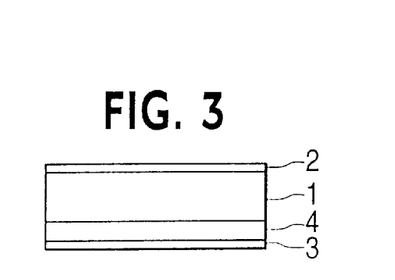
FIG. 3 shows the active substance-containing, pressure sensitive hot-melt adhesive (1); the side facing the substrate is combined with a lipophilic element (4) which does not contain any active substance and serves as controlling membrane.
Figure 4:
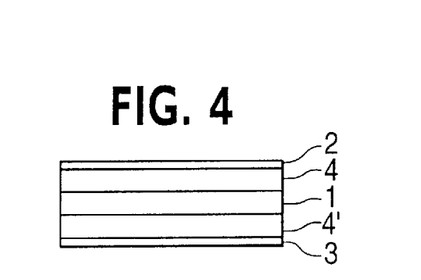
FIG. 4 also shows a multi-layer composite wherein an active substance-containing, hydrophilic pressure sensitive hot-melt adhesive (1) is enclosed in a sandwich-type manner by two lipophilic elements (4', 4"). Again, this arrangement is covered by backing layer (2) and protective layer (3).
Figure 5A:
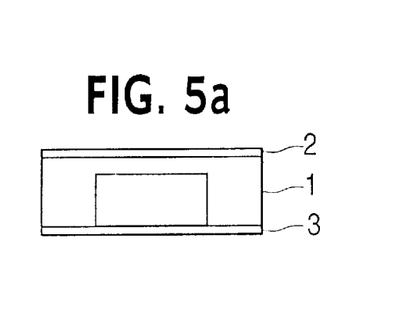
FIGS. 5a and 5b show an embodiment of the hydrophilic pressure sensitive hot-melt adhesive (1), wherein it is surrounded by a lipophilic element (4) at least partially, or wherein it surrounds a lipophilic element at least partially. Both elements may comprise active substances.
Figure 5B:
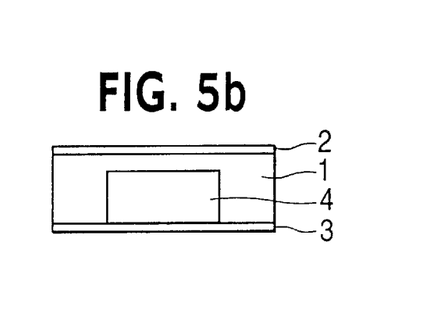
Figure 6A:
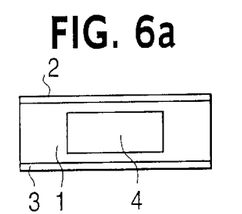
FIG. 6a shows another embodiment wherein the hydrophilic pressure sensitive hot-melt adhesive (1) acting as an active substance-containing controlling element encloses an additional lipophilic active substance storage (4)
Figure 6B:
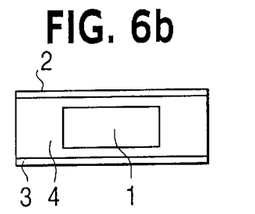
in FIG. 6b, the hydrophilic pressure sensitive hot-melt adhesive (1) acting as storing element is completely embedded in a lipophilic film (4) acting as controlling element; one surface of the lipophilic storing element (4) or of the pressure sensitive hot-melt adhesive (1) acting as storage may also be immediately adjacent to the backing layer (2) (FIGS. 6c and 6d).
Figure 6C:
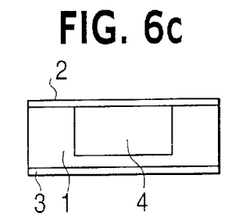
Figure 6D:
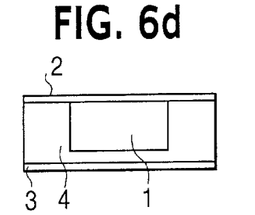
Figure 7A:
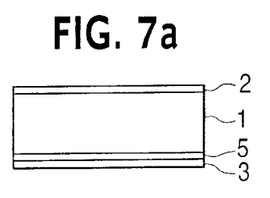
FIGS. 7a, 7b, and 7c represent embodiments of a hydrophilic pressure sensitive hot-melt adhesive (1) having an adhesive layer (5); said adhesive layer covers the whole hydrophilic pressure sensitive hot-melt adhesive continuously (FIG. 7a), or discontinuously, i.e., in an interrupted manner (FIG. 7b), or parts of the hydrophilic pressure sensitive hot-melt adhesive (FIG. 7c).
Figure 7B:
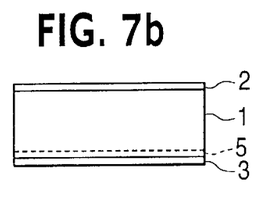
Figure 7C:
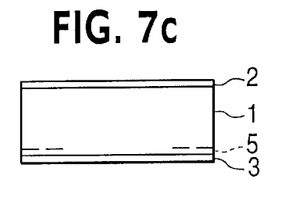

The device according to the present invention as well as the hydrophilic pressure sensitive hot-melt adhesive may have a multilayer structure. For instance, at least two hydrophilic pressure sensitive hot-melt adhesives may be joined according to known methods to form a composite (FIG. 2). It is also possible to join one or more hydrophilic pressure sensitive hot-melt adhesives with one or more lipophilic elements to form a composite of any structure desired (FIGS. 3/4). For example, such elements may serve as controlling elements, storing elements, permeable or impermeable separating elements. The individual elements of the composite may be a coherent, interconnected unit; they may also be separated into segments which are surrounded or enclosed by the element lying above or below (FIGS. 5/6). For instance, a lipophilic adhesive layer may be applied to a hydrophilic pressure sensitive hot-melt adhesive either continuously or in the form of points or diamonds, wherein the pressure sensitive hot-melt adhesive may fill the spaces between the lipophilic segments (FIG. 7). According to another embodiment, the hydrophilic pressure sensitive hot-melt adhesive is combined with textile fabrics, fibrous structures, and/or natural or synthetic foams. In this multi-layer composite the individual layers may be produced separately according to known methods and then be joined. The layers may also penetrate each other, for example, when the molten mass of the hydrophilic pressure sensitive hot-melt adhesive is applied on a fabric, fibrous structure, or foam prior to the formation of the film, and the formation of the film takes place only after the mass has been soaked into the fabric or the foam.

Figure 8A:
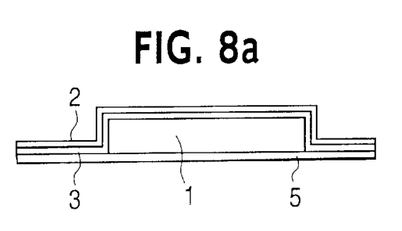
FIGS. 8a and 8b show devices wherein a hydrophilic pressure sensitive hot-melt adhesive (1) is covered with a protective layer (3) and a backing layer (2) which has larger dimensions than the hydrophilic pressure sensitive hot-melt adhesive (1) and which is completely (FIG. 8a) or partially (FIG. 8b) coated with an adhesive film (5).
Figure 8B:
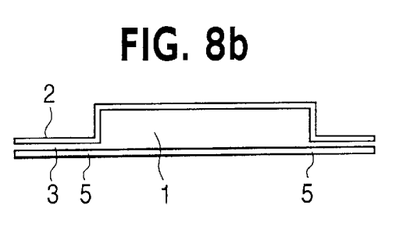

Fixation of the device according to the present invention at the place of use is generally effected by the hydrophilic pressure sensitive hot-melt adhesive of the device. Another possibility of fixing the device according to the present invention to the place of application is that the backing layer has larger dimensions than the part consisting of hydrophilic pressure sensitive hot-melt adhesive and that at least the projecting portions of the backing layer are provided with an additional adhesive layer (FIG. 8).

The last-mentioned embodiments of the device according to the present invention wherein the hydrophilic pressure sensitive hot-melt adhesive is present in a multi-layer, multi-part form or in combination with separating and controlling elements, have the advantage that parts of different composition may be combined with each other. The use of different adjuvants or different active substance concentrations in the individual elements shall provide a release behavior of the active substance/s which is required for the application and that cannot be achieved, for example, by a single-layer structure of the hydrophilic pressure sensitive hot-melt adhesive.

BRIEF DESCRIPTION OF THE DRAWINGS

FIGS. 1 to 8 illustrating the invention will be described in more detail in the following:

In addition to the already presented Examples 1 to 3 which basically describe the device according to the present invention for the release of substances from hydrophilic pressure sensitive hot-melt adhesives, the following Examples are meant to describe formulation alternatives, embodiments and application possibilities of the device mentioned in the main claim; however, this listing can by no means be extensive:

EXAMPLE 4

25 parts of pantothenyl alcohol are melted at 90° C. 10 parts of sodium alginate and 10 parts of gelatin are slowly stirred into the melt until a uniform distribution is achieved (melt A).

25 parts of hydroabietyl alcohol are melted separately at 125° C. 10 parts of an ethyl-vinyl acetate-copolymer having a vinyl acetate content of 28%, 10 parts of a polyalkadiene having a monomer chain length of C4 to C5, and 10 parts of acetylsalicylic acid are slowly stirred into the hydroabietyl alcohol melt at 120° C. until a clear melt results (melt B).

Melt B is cooled to 90° C. under stirring; at 90° C. it is slowly stirred into melt A until a uniform distribution is achieved. The pressure sensitive hot-melt adhesive is then spread on a siliconized paper composite at a mass per unit area of 300 g/m$^2$ by means of knife coating. After cooling, a polyester sheet is laminated thereon, and devices having an area of 30 cm$^2$ are punched from the laminate; the devices contain 90 mg of acetylsalicylic acid.

EXAMPLE 5

20 parts of pantothenyl alcohol are melted at 90° C. 10 parts of glycerol, 4 parts of ethylcellulose, 4 parts of lidocaine, and 4 parts of prilocaine are slowly stirred into the melt up to an even distribution (melt A).

At room temperature, 18 parts of gelatin, 10 parts of polyvinylpyrrolidone, 5 parts of sodium carboxymethyl starch, and 5 parts of saccharose are made into a paste with 20 parts of water, homogenized intensively until an even distribution is achieved, and then heated to 90° C. under stirring (melt B).

At 90° C., melt B is slowly stirred into melt A up to a uniform distribution. The pressure sensitive hot-melt adhesive is then spread at a mass per unit area of 500 g/m$^2$ on a siliconized paper composite by means of knife coating. After cooling, a polyester sheet is laminated thereon. Devices having a surface of 25 cm$^2$ are punched from this laminate; the devices comprise 50 mg of lidocaine and 50 mg of prilocaine.

EXAMPLE 6

25 parts of pantothenyl alcohol are melted at 90° C. 12.5 parts of sodium alginate and 12.5 parts of gelatin are slowly stirred into the melt until a uniform distribution is achieved (melt A).

Separately, 25 parts of hydroabietyl alcohol are melted at 125° C. 10 parts of an ethylene-vinyl acetate-copolymer having a vinyl acetate content of 28%, 10 parts of a polyalkadiene having the monomer chain length C4 to C5, 2.5 parts of lidocaine, and 2.5 parts of prilocaine are slowly stirred into the hydroabietyl alcohol melt at 120° C. until a clear melt results (melt B). Under stirring to 90° C., melt B is slowly stirred into melt A up to a uniform distribution. The pressure sensitive hot-melt adhesive is then spread on a siliconized paper composite at a mass per unit area of 500 mg/m² by means of knife coating. After cooling, a polyester sheet is laminated thereon, and devices having an area of 25 cm² are punched from the laminate; the devices comprise 31.25 mg of lidocaine and 31.25 mg of prilocaine.

EXAMPLE 7

20 parts of pantothenyl alcohol are melted at 90° C. 10 parts of glycerol, 1 part of ethylcellulose, and 5 parts of tobacco powder are slowly stirred into the melt until an even distribution is achieved (melt A).

At room temperature, 18 parts of gelatin, 10 parts of polyvinylpyrrolidone, 5 parts of sodium carboxymethyl starch, and 11 parts of saccharose are made into a paste using 20 parts of water, homogenized intensively until an even distribution is achieved, and then heated to 90° C. under stirring (melt B).

At 90° C., melt B is slowly stirred into melt A up to a uniform distribution. The pressure sensitive hot-melt adhesive is then spread at a mass per unit area of 600 g/m² on a siliconized paper composite by means of knife coating. After cooling, a polyester sheet is laminated thereon. Devices having an area of 20 cm² are punched from this laminate; the devices comprise 60 mg of tobacco powder.

EXAMPLE 8

50 parts of pantothenyl alcohol are melted at 90° C. 25 parts of polyethylene glycol having a molecular weight of 15,000, 20 parts of sodium alginate, and 5 parts of an aqueous chlorohexidine digluconate solution are slowly stirred into this melt until an even distribution is achieved.

Then, the pressure sensitive hot-melt adhesive is spread on a siliconized paper composite at a mass per unit area of 300 g/m² by means of knife coating. After cooling, a polyester sheet is laminated thereon. Devices having an area of 200 cm² and containing 300 mg chlorohexidine digluconate solution are punched from this laminate. The device is used topically for the disinfection of the skin in case of bacterially caused skin diseases or for the disinfection of infected wounds.

EXAMPLE 9

20 parts of pantothenyl alcohol are melted at 90° C. 16 parts of sodium alginate, 9 parts of salicylic acid, and 2 parts of ethylcellulose are stirred into the melt until an even distribution is achieved (melt A).

Separately, 28 parts of hydroabietyl alcohol, 15 parts of an ethylene-vinyl-acetate copolymer having a vinyl acetate content of 28%, and 10 parts of a polyalkadiene having a monomer chain length of C4 to C5 are melted at 125° C. (melt B).

Melt B is cooled to 90° C. under stirring; at 90° C. it is slowly stirred into melt A until a uniform distribution is achieved. The pressure sensitive hot-melt adhesive is then spread on a siliconized paper composite at a mass per unit area of 1,400 g/m² by means of a coating knife; prior to cooling, an open-cell polyurethane foam of 2 mm the back of which is sealed with a polyurethane sheet of a thickness of 20 µm is placed on the still soft mass under slight pressure.

After cooling, oval devices having an area of 15 cm² are punched from this composite. Because of the keratolytic action of the salicylic acid contained in the pressure sensitive hot-melt adhesive, these devices comprising a pressure-sensitive-hot-melt-adhesive-foam-composite are used, for example, for the topical treatment of corns. The combination with foam simultaneously reduces the pressure on the site to the treated.

EXAMPLE 10

20 parts of pantothenyl alcohol are melted at 90° C. 10 parts of glycerol and 1 part of ethylcellulose are slowly stirred into the melt up to an even distribution (melt A).

At room temperature, 18 parts of gelatin, 10 parts of polyvinylpyrrolidone, 5 parts of sodium carboxymethyl starch, 10 parts of saccharose, 2 parts of St. John's wort tincture, 2 parts of cone flower tincture, and 2 parts of chamomile extract are made into a paste using 20 parts of water, intensively homogenized until an even distribution is obtained, and then heated to 90° C. under stirring (melt B).

At 90° C., melt B is slowly stirred into melt A until an even distribution is achieved. Then, the pressure sensitive hot-melt adhesive is spread on a siliconized HDPE-film at a mass per unit area of 600 g/m² by means of knife coating; after cooling, a polyester sheet is laminated thereon. Circular pieces having an area of 10 cm² are punched from this pressure sensitive hot-melt adhesive-polyester-composite. The polyester side of these pieces is laminated on the adhesive layer of an acrylate-coated polyester sheet. After removal of the siliconized HDPE-film, a siliconized paper composite is laminated thereto; circular devices having an area of 25 cm² are punched such that the hydrophilic pressure sensitive hot-melt adhesive is in a central position, in the middle of the device. Thus, the device consists of a backing layer of polyester, an adhesive layer for fixation on the skin, a separating layer of polyester to prevent migration of substances from the hydrophilic pressure sensitive hot-melt adhesive into the lipophilic adhesive layer, the tincture- or extract-containing hydrophilic pressure sensitive hot-melt adhesive, and a protective layer to be removed prior to application.

The device is used locally, for example, for the treatment of first-degree burns, contused lesions, and slow-healing, superficial wounds.

EXAMPLE 11

18 parts of pantothenyl alcohol are melted at 90° C. 8 parts of glycerol and 4 parts of ethylcellulose are slowly stirred into the melt until an even distribution results (melt A).

20 parts of gelatin, 10 parts of polyvinylpyrrolidone, 5 parts of sodium carboxymethyl starch, 10 parts of saccharose, and 5 parts of a 4% collagen dispersion are made into a paste at room temperature with 20 parts of water, intensively homogenized up to a uniform distribution, and then heated to 90° C. under stirring (melt B).

At 90° C., melt B is slowly stirred into melt A up to an even distribution. The pressure sensitive hot-melt adhesive is then spread on a siliconized paper composite at a mass per unit area of 1,500 g/m² by means of knife coating; after cooling, a polyurethane sheet is laminated thereon. Devices of 100 cm² are punched from the laminate; they comprise 30 mg of pure collagen. The device is used for the release of the healing-promoting collagen from the hydrophilic pressure sensitive hot-melt adhesive to slow-healing problematic wounds, e.g., varicose ulcera.

EXAMPLE 12

20 parts of pantothenyl alcohol are melted at 90° C. 18 parts of sodium carboxymethylcellulose are slowly stirred into the melt up to an even distribution (melt A).

32 parts of hydroabietyl alcohol are melted separately at 125° C. 16 parts of an ethylene-vinyl-acetate-copolymer having a vinyl acetate content of 28%, 10 parts of a polyalkadiene having a monomer chain length of C4 to C5, 2 parts of ethylcellulose, 1 part of chamomile oil, and 1 part of chlorophyll are slowly stirred into said hydroabietyl melt at 120° C. until a clear melt results (melt B).

Melt B is cooled under stirring to 90° C. and slowly stirred into melt A at 90° C. up to an even distribution. Then, the pressure sensitive hot-melt adhesive is spread on a siliconized paper composite at a mass per unit area of 1,000 g/m² by means of knife coating. After cooling, a polyurethane sheet is laminated thereon. Devices having an area of 25 cm² are punched from the laminate. The devices comprise 25 mg of chamomile oil and 25 mg of chlorophyll and are used, for example, for the treatment of pressure sores and chafed sites.

EXAMPLE 13

20 parts of pantothenyl alcohol are melted at 90° C. 21 parts of sodium carboxymethyl starch and 2 parts of a glycolic extract of fucus vesicolosus are stirred into the melt up to an even distribution (melt A).

30 parts of hydroabietyl alcohol, 15 parts of an ethyl-vinyl-acetate-copolymer having a vinyl acetate content of 28%, 10 parts of a polyalkadiene having the monomer chain length C4 to C5, 1 part of ethylcellulose, and 1 part of vitamin E are melted separately at 125° C. (melt B).

Melt B is cooled to 90° C. under stirring and slowly stirred into melt A at 90° C. up to an even distribution. Then, the pressure sensitive hot-melt adhesive is spread on a siliconized polyester sheet at a mass per unit area of 300 g/m² by means of knife coating. After cooling, a polyurethane sheet is laminated thereon. Devices having a surface of 10 cm² are punched from the laminate. The devices comprise 6 mg of fucus extract and 3 mg of vitamin E; they are used, for example, for the topical treatment of skin areas damaged by exposure to the sun or by environmental toxicants in order to bind moisture in the skin and to achieve an effective cell protection against external influences.

EXAMPLE 14

20 parts of pantothenyl alcohol are melted at 90° C. 10 parts of glycerol and 1 part of ethylcellulose are slowly stirred into the melt until an even distribution results (melt A).

18 parts of gelatin, 10 parts of polyvinylpyrrolidone, 5 parts of sodium carboxymethyl starch, 10 parts of saccharose, 3 parts of tincture of arnica, and 3 parts of calendula tincture are made into a paste at room temperature using 20 parts of water, intensively homogenized until a uniform distribution is achieved, and then heated to 90° C. under stirring (melt B).

At 90° C., melt B is slowly stirred into melt A up to an even distribution. The pressure sensitive hot-melt adhesive is then spread on a siliconized paper composite at a mass per unit area of 400 g/m² by means of knife coating; after cooling, a polyester sheet is laminated thereon. Devices of 50 cm² are punched from the laminate; they comprise 60 mg of arnica tincture and 60 mg of calendula tincture. The devices are used, for example, for the intradermal treatment of sprains, contusions, and haemorrhages.

EXAMPLE 15

19 parts of pantothenyl alcohol are melted at 90° C. 8 parts of glycerol and 4 parts of ethylcellulose are slowly stirred into the melt until an even distribution results (melt A).

At room temperature, 20 parts of gelatin, 10 parts of polyvinylpyrrolidone, 5 parts of sodium carboxymethyl starch, 9 parts of saccharose, and 5 parts of an aqueous extract of green tea are made into a paste using 20 parts of water, intensively homogenized until a uniform distribution is achieved, and then heated to 90° C. under stirring (melt B).

At 90° C., melt B is slowly stirred into melt A up to an even distribution. Then, the pressure sensitive hot-melt adhesive is spread on a siliconized polyester sheet at a mass per unit area of 400 g/m² by means of knife coating; after cooling, a polyurethane sheet is laminated thereon. Devices having an area of 100 cm² are punched from the laminate. The devices comprise 20 mg of tea extract; when applied to the skin they are used to a achieve a stimulating effect on the circulatory system by the transdermal release of caffeine, which is the main component of the extract.

EXAMPLE 16

20 parts of pantothenyl alcohol are melted at 90° C. 10 parts of glycerol, 1 part of ethylcellulose, and 5 parts of hop extract are slowly stirred into the melt until an even distribution results (melt A).

18 parts of gelatin, 10 parts of polyvinylpyrrolidone, 5 parts of sodium carboxymethyl starch, and 11 parts of saccharose are made into a paste at room temperature using 20 parts of water, intensively homogenized until a uniform distribution is achieved, and then heated to 90° C. under stirring (melt B).

At 90° C., melt B is slowly stirred into melt A up to an even distribution. The pressure sensitive hot-melt adhesive is then spread on a siliconized paper composite at a mass per unit area of 300 g/m² by means of knife coating and temporarily covered with a siliconized HDPE-sheet.

Separately, a second hydrophilic pressure sensitive hot-melt adhesive is manufactured in accordance with the above formulation; instead of hop extract, it contains 5 parts of valerian extract. After spreading on a siliconized paper composite and cooling, this hydrophilic pressure sensitive hot-melt adhesive is laminated on the pressure sensitive hot-melt adhesive comprising the hop extract; prior to that the temporary HDPE-sheet is stripped off. After removal of the siliconized paper composite from the valerian-extract-layer, a polyurethane layer is laminated on this layer.

Devices with an area of 30 cm² are punched from this multi-layer composite; they comprise 45 mg of hop extract in the pressure sensitive hot-melt adhesive facing the protective layer, and 45 mg of valerian extract in the pressure sensitive hot-melt adhesive facing the backing layer.

When applied to the skin, these devices are used to achieve a calmative effect, for example, in stress situations, by the transdermal release of the sedative components of the valerian and hop.

EXAMPLE 17

24 parts of pantothenyl alcohol are melted at 90° C. 10 parts of glycerol and 2 parts of ethylcellulose are slowly stirred into the melt until a uniform distribution results (melt A).

18 parts of sodium alginate, 10 parts of polyvinylpyrrolidone, 5 parts of sodium carboxymethyl starch, and 11 parts of saccharose are made into a paste at room temperature using 20 parts of water, intensively homogenized until a uniform distribution is achieved, and then heated to 90° C. under stirring (melt B).

At 90° C., melt B is slowly stirred into melt A up to an even distribution. The pressure sensitive hot-melt adhesive is then spread on a siliconized paper composite at a mass per unit area of 200 g/m$^2$ by means of knife coating; after cooling a siliconized HDPE intermediate cover is laminated thereon. The composite is cut such that narrow rolls having a width of 13 cm are obtained. The intermediate cover is removed from such a narrow roll, and a mixture comprising 1 ml of eucalyptus oil and 1 of ml pine-needle oil is applied on the pressure sensitive hot-melt adhesive in a dotlike manner on areas of 6×13 cm. After removal of the intermediate cover, a second hydrophilic pressure sensitive hot-melt adhesive having a width of 13 cm is laminated on said layer. After removal of one of the siliconized paper protective layers, a microporous polyester backing layer is laminated.

Devices of 6×13 cm are punched and sealed tightly. After uniform distribution of the essential oils in the pressure sensitive hot-melt adhesive by means of diffusion, the device may be used for colds, e.g., by sticking it on the skin in the upper chest region. When the device is heated to body temperature, the essential oils which are released via the micro-porous backing layer and are then inhaled can develop their alleviating effect.

What is claimed is:

1. A self-adhesive product for application to intact skin which comprises
    a water-free pressure sensitive adhesive for the release of a substance to or through the skin, and
    a substance to be released, said substance being distributed within said pressure sensitive adhesive,
    wherein said pressure sensitive adhesive is a pressure sensitive hot-melt adhesive prepared by melt mixing at a temperature of between 40 and 150° C. a mixture comprising
        at least one water-soluble or water-swellable polymer, and
        at least one water-soluble meltable adhesive resin.

2. A product according to claim 1, wherein said substance is uniformly distributed within said pressure-sensitive adhesive.

3. A product according to claim 1, wherein said substance is non-uniformly distributed within said pressure-sensitive adhesive.

4. A product according to claim 1, wherein the pressure-sensitive hot-melt adhesive comprises water-soluble, ropy, low-viscous tacky substance in combination with hydrophilic polymer forming coherent layers of excellent cohesion.

5. A product according to claim 1, wherein the pressure-sensitive hot-melt adhesive is hydrophilic and comprises at least one water-soluble or water-swellable polymer and at least one water-soluble, meltable adhesive resin.

6. A product according to claim 1, wherein the pressure sensitive hot-melt adhesive is hydrophilic and is melt mixed at a temperature between 80 and 120° C.

7. A product according to claim 1, wherein the water-soluble meltable adhesive resin component is pantothenyl alcohol, honey, a low-molecular weight sugar, an ester of a low-molecular weight sugar or mixtures thereof.

8. A product according to claim 1, wherein the pressure-sensitive adhesive hot-melt adhesive is hydrophilic and contains, as water-soluble or water-swellable polymer, at least one member of the group consisting of gelatin, sodium alginate, pectin, carrageenan, xanthan, cellulose derivatives, starch and starch derivatives, galactomannan and galactomannan derivatives, polyvinyl alcohol, polyvinylpyrrolidone, vinyl-pyrrolidone-vinyl-acetate copolymers, polyethylene glycols and polypropylene glycols.

9. A product according to claim 1, wherein the substance to be released is acetylsalicylic acid.

10. A product according to claim 1, wherein the substance to be released is a steroid hormone.

11. A product according to claim 1, wherein a eutectic mixture of lidocaine and prilocaine is the substance to be released.

12. A product according to claim 1, wherein at least one vegetable preparation is the substance to be released.

13. A product according to claim 12, wherein the vegetable preparation is an extract or tincture.

14. A product according to claim 1, wherein a triturated plant portion is the substance to be released.

15. A product according to claim 14, wherein the triturated plant portion is tobacco powder.

16. A product according to claim 1, wherein the pressure-sensitive hot-melt adhesive is hydrophilic and comprises a lipophilic phase.

17. A product according to claim 1, wherein the pressure-sensitive hot-melt adhesive is hydrophilic and comprises at least one adjuvant selected from the group consisting of humectants, softening agents, penetration enhancers, preservatives, disinfectants, pH-regulators, antioxidants, active substance stabilizers, emulsion stabilizers, odorous substances, dyes, inert fillers, oils, fats, and waxes.

18. A product according to claim 1, comprising a flexible backing layer, an active substance-containing, hydrophilic pressure-sensitive hot-melt adhesive connected thereto, in the absence of other controlling mechanisms a membrane controlling the release of the substances, optionally a pressure-sensitive adhesive means connected to the membrane for the fixation of the product to the skin, and a protective layer which covers an adhesive surface of the product facing the skin and which is removed prior to the application of the product.

19. A product according to claim 18, wherein the backing layer is permeable to highly volatile substances.

20. A product according to claim 1, wherein the pressure-sensitive hot-melt adhesive is hydrophilic and has a porous structure.

21. A product according to claim 1, wherein the substance-releasing portion has a multi-layer or multi-part structure wherein the individual layers or parts have the same or different composition.

22. A product according to claim 1, wherein the product is at least partially biodegradable.

23. A method of using a product according to claim 1, which comprises applying said product to the skin of a human or animal.

24. A method of using a product according to claim 1, which comprises applying said product to a plant.

* * * * *